United States Patent
Kruip (10) Patent No.: US 9,526,918 B2
(45) Date of Patent: Dec. 27, 2016

(54) COMBINED MRI AND RADIATION THERAPY SYSTEM

(71) Applicant: Marcel Kruip, Oxfordshire (GB)

(72) Inventor: Marcel Kruip, Oxfordshire (GB)

(73) Assignee: Siemens PLC, Camberley (GB)

( * ) Notice: Subject to any disclaimer, the term of this patent is extended or adjusted under 35 U.S.C. 154(b) by 563 days.

(21) Appl. No.: 14/077,363

(22) Filed: Nov. 12, 2013

(65) Prior Publication Data

US 2014/0135615 A1   May 15, 2014

(30) Foreign Application Priority Data

Nov. 12, 2012 (GB) .................................. 1220271.9

(51) Int. Cl.
| | |
|---|---|
| *G01V 3/00* | (2006.01) |
| *A61N 5/10* | (2006.01) |
| *A61B 5/055* | (2006.01) |
| *G01R 33/48* | (2006.01) |
| *G01R 33/421* | (2006.01) |

(52) U.S. Cl.
CPC ............ *A61N 5/1081* (2013.01); *A61B 5/055* (2013.01); *A61N 5/1049* (2013.01); *G01R 33/4808* (2013.01); *A61N 2005/1055* (2013.01); *G01R 33/421* (2013.01)

(58) Field of Classification Search
CPC ............... A61N 5/1081; A61N 5/1049; A61N 2005/1055; A61B 5/055; G01R 33/4808; G01R 33/421
USPC ........................................................ 324/307
See application file for complete search history.

(56) References Cited

U.S. PATENT DOCUMENTS

| | | | | |
|---|---|---|---|---|
| 4,924,185 | A * | 5/1990 | Matsutani | G01R 33/421 324/319 |
| 6,366,798 | B2 * | 4/2002 | Green | A61N 5/1042 378/65 |
| 8,836,332 | B2 * | 9/2014 | Shvartsman | G01R 33/421 324/309 |
| 8,981,779 | B2 * | 3/2015 | Shvartsman | G01R 33/3642 324/319 |
| 2008/0100295 | A1 * | 5/2008 | Nakayama | G01R 33/3873 324/318 |

(Continued)

FOREIGN PATENT DOCUMENTS

| | | | | |
|---|---|---|---|---|
| GB | 2382512 A | * | 5/2003 | ............ A61B 5/055 |
| GB | 2484529 | | 4/2012 | |

(Continued)

*Primary Examiner* — Susan Lee
(74) *Attorney, Agent, or Firm* — Schiff Hardin LLP (57) ABSTRACT

A combined MRI and radiation therapy system has MRI imaging equipment and radiation therapy equipment. The MRI imaging equipment includes a shielded solenoidal magnet including a number of main magnet coils arranged coaxially along an axis, and a shielding arrangement arranged coaxially with the axis, at a greater radius from the axis than the main magnet coils. The radiation therapy equipment includes a LINAC assembly, that includes a linear electron accelerator arranged with an electron beam path parallel to the axis, and electron beam deflection arrangement and a target for generating a beam of therapeutic radiation. The linear electron accelerator is located at a position radially between the main magnet coils and the shielding arrangement.

12 Claims, 4 Drawing Sheets

(56) References Cited

U.S. PATENT DOCUMENTS

| | | | |
|---|---|---|---|
| 2008/0208036 A1* | 8/2008 | Amies | A61N 5/1049 600/411 |
| 2011/0196226 A1* | 8/2011 | Gross | A61B 5/055 600/411 |
| 2011/0213239 A1 | 9/2011 | Amies et al. | |

FOREIGN PATENT DOCUMENTS

| | | | | |
|---|---|---|---|---|
| GB | 2491363 | | 12/2012 | |
| SE | 2424281 A | * | 9/2006 | A61N 5/1049 |
| WO | 03/008986 | | 1/2003 | |
| WO | WO 2011008969 A1 | * | 1/2011 | G01R 33/421 |
| WO | 2011/127946 | | 10/2011 | |
| WO | 2012/049466 | | 4/2012 | |
| WO | 2012/164527 | | 12/2012 | |

* cited by examiner

COMBINED MRI AND RADIATION THERAPY SYSTEM

BACKGROUND OF THE INVENTION

Field of the Invention

The present invention relates to combined MRI and radiation therapy equipment.

Description of the Prior Art

Certain examples of combined MRI and radiation therapy equipment are known, but suffer from certain drawbacks. The present invention addresses at least some of those drawbacks.

Radiation therapy typically uses gamma radiation, or similar, to target cancerous tissues in a patient. Such radiation may be generated either using an electron beam generated by an accelerator and aimed at a suitable target, or a radiation source containing a suitable radioactive isotope, such as cobalt-60.

The use of a cobalt-60 source involves difficulties in storage, and prevention of over-exposure by operators. Screening of such sources can only be achieved by significant amounts of dense material such as lead or tungsten. Such sources are simple and are not affected by magnetic fields such as would be encountered in a combined MRI and radiation therapy system. The radiation produced is however of relatively low energy, and cannot be intensity-modulated.

Radiation generation by electron beam acceleration onto a suitable target has the advantages of being able to produce higher-energy photons, and may be intensity modulated.

The accelerators required to produce an electron beam, typically linear accelerators, are very sensitive to transverse magnetic fields, which makes their incorporation into MRI equipment difficult. The magnetic field deflects the path of the electron beam within the accelerators, destroying the efficacy of such radiation sources.

An example arrangement which allows a linear electron accelerator (LINAC) to be built into an MRI system and used for combined MRI and radiation therapy is known from WO2003008986 and uses a radially-aligned LINAC. The LINAC and its associated target are arranged to project a radiation beam through an aperture or transparent window in a cryostat, between coils of a superconducting MRI magnet. The radially-aligned LINAC is arranged on the mid-plane of the magnet, and requires a lot of space around the magnet, making it impractical for many installations. The magnetic field of the main magnet is transverse to the LINAC, and interferes with the electron beam path. Only relatively low main magnet field strength (flux density) can be tolerated.

A more compact arrangement of combined MRI and radiation therapy equipment is described in US Patent publication US2011/0213239A1, International Patent publication WO2012049466 and UK Patent GB2484529. In this arrangement, the linear accelerator (LINAC) is arranged parallel to the axis of the magnet and is situated between gradient coils and the main magnet field coils of an MRI system. Beam steering arrangements are provided to deflect the generated electron beam from an axial path, parallel to the axis of the magnet, to a radial path, perpendicular to the axis, and then onto a suitable target. The LINAC and target are accordingly immersed in a relatively strong magnetic field.

Figure 1:
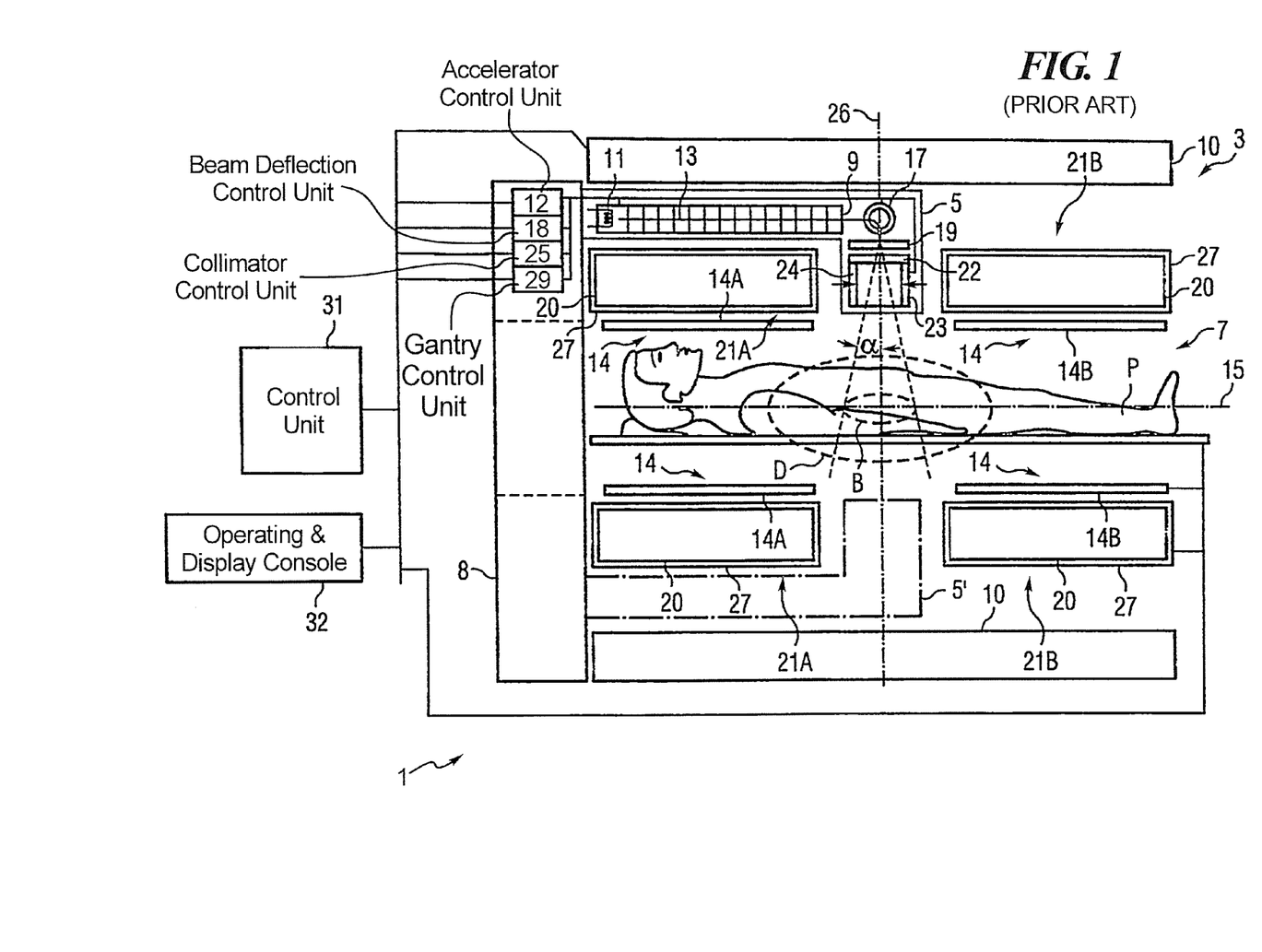
FIG. 1 illustrates a combined MRI/radiation therapy system of the prior art.

FIG. 1 corresponds to FIG. 1 of WO2012049466, US2011/0213239A1 and GB2484529. It shows a schematic representation of a conventional combined radiation therapy and magnetic resonance unit 1 with a magnetic resonance imaging part 3 and a radiation therapy part 5. The magnetic resonance imaging part 3 includes a main magnet 10, a gradient coil system having two (in this case symmetrical) partial gradient coils 21A, 21B, radio-frequency coils 14, for example two parts of a body coil 14A, 14B, and a patient bed 6. All these components of the magnetic resonance imaging part 3 are connected to a control unit 31 and an operating and display console 32.

Both the main magnet 10 and the partial gradient coils 21A, 21B are essentially shaped like a hollow cylinder and arranged coaxially around the horizontal axis 15. The inner shell of the main magnet 10 limits in radial direction (perpendicular to the axis 15) a cylinder-shaped interior 7, in which the radiation therapy part 5, the gradient system, high-frequency coils 14 and the patient bed 6 are arranged. More precisely the radiation therapy part 5 is located in the interior 7 between a radially outer side of the gradient coil system 21A and 21B and a radially inwardly facing surface of a housing of the main magnet 10.

In addition to the magnet coils, the main magnet 10 comprises further structural elements, such as supports, housing etc., and generates a homogenous main magnetic field necessary for magnetic resonance imaging. In the example shown, the direction of the main magnetic field is parallel to the horizontal axis 15. High-frequency coils 14 are used to excite nuclear spins in the patient. The signals emitted by the excited nuclear spins are received by the high-frequency coils 14.

The axially spaced-apart partial gradient coils 21A, 21B in each case include gradient coils 20, which are in each case completely enclosed by a shield 27. The gradient coil 20 has supports and individual gradient coils that generate magnetic gradient fields for selective layer excitation and for location-coding of the magnetic resonance signals in three spatial directions.

The radiation therapy part 5 is arranged on a gantry 8 and comprises a linear electron accelerator (LINAC) 9, a beam deflection arrangement 17, a target anode 19, a homogenizing body 22 and a collimator 23. The gantry 8 can feature a through-hole (broken lines), by which access to the magnetic resonance imaging 3 part is possible, through the gantry.

The LINAC 9 has an electron source 11, for example a tungsten cathode, which generates an electron beam 13, which is accelerated parallel to the axis 15 of the main magnet 10. If the LINAC 9 generates pulsed electron beams 13, it can be built more compactly than one designed to provide a continuous electron beam. The LINAC 9 for example may generate electron beam pulses with a length of 5 µs every 5 ms.

The electrons of the electron beam 13 are accelerated by electric alternating fields in cylinder-shaped hollow conductors of the LINAC 9. The electrons of the electron beam 13 are accelerated to energies up to a magnitude of several MeV. The LINAC 9 is connected to an accelerator control unit 12 to control the alternating fields and the electron source 11.

The electron beam 13 leaves the LINAC 9 at the end opposite the electron source and is deflected by the beam deflection arrangement 17 through 90° radially inward towards axis 15. For this purpose the beam deflection arrangement 17 may have a magnet configured as an electromagnet made of non-ferromagnetic materials to prevent undesired interaction with the surrounding magnetic fields.

To be able to deflect the pulsed electron beam 13 in a small space, the beam deflection arrangement 17 must generate strong magnetic fields. To reduce the power loss, the magnetic field of the beam deflection arrangement 17 is a pulsed electro-magnetic field which is synchronized with the pulsed electron beam 13. For this purpose the beam deflection arrangement 17 is connected to a beam deflection control unit 18 which is also connected to the accelerator control unit 12.

The deflected electron beam 13 hits the target anode 19 and generates a radiation beam that emerges from the target anode in the beam elongation along a beam path. The radiation beam is homogenized by the homogenizing body 22.

The collimator 23 is arranged in an annular slot between the distanced partial gradient coils 21A, 21B in the beam path after the target anode 19. The proximity to the irradiation target thus achieved improves the radiation luminance and the effectiveness of the collimator 23.

The collimator 23 enables the direction of the radiation beam and the cross-section of the radiation beam to be influenced. For this purpose the collimator 23 preferably incorporates moveable adjusters 24, which permit the radiation beam to pass only in a certain direction, e.g. only parallel to the radial direction 26 or up to an angle α away from the beam axis 26, and with a certain cross-section. It is also possible to set the adjusters 24 of the collimator 23 in such a way that no radiation beams can pass parallel to the radial beam axis direction 26 and only angled radiation beams at certain angles from the radial direction 26 can pass through. To control the adjusters 24, the collimator 23 is connected to a collimator control unit 25. Such collimators are adequately known. By way of example, reference can be made to multi-leaf collimators. They make it possible to perform intensity modulated radiation therapy (IMRT), in which the size, shape and intensity of the radiation beam can be optimally adapted to the irradiation target. In particular IMRT also enables the irradiation center to be positioned outside the rotational axis of the radiation therapy device.

The radiation beam penetrates the examination subject, in this case the patient P, and the radiation beam path runs through a diagnosis (imaging) volume D of the magnetic resonance imaging part 3. To minimize the local dose of radiation outside the irradiation target volume, the radiation therapy part rotates around the axis 15 of the main magnetic field. As a result, the full dose is applied only in the irradiation center B. The collimator 23 constantly adapts the cross-section of the radiation beam to the actual outline of the irradiation target even during rotation. The gantry 8 is configured for rotation of the radiation therapy part. A gantry control unit 29 controls the movement of the radiation therapy part 5. As an example the radiation therapy part 5 is shown as radiation therapy part 5' after rotation through 180°.

The gantry control unit 29, the collimator control unit 25, the beam deflection control unit 18, the accelerator control unit 12 and the control unit 31 are connected to each other so that the diagnosis data collected by the magnetic resonance imaging part, for example the three-dimensional shape of the irradiation target, the rotational position of the radiation therapy part, as well as the collimator settings with regard to cross-section and direction of the radiation beam and the generation of pulsed beams described above can be coordinated with each other.

The patient bed 6 is preferably moveable in three spatial directions so that the target area of the irradiation can be positioned precisely in the irradiation center B. For this purpose the control unit 31 is expediently configured for controlling a movement of the patient bed.

This known arrangement, however, suffers from certain disadvantages. By locating the LINAC 9 and the target 19 within the main magnet 10, the coils of the main magnet must be of relatively large diameter, and the LINAC and target must be located close to the main magnet coils, in order to keep the overall size of the system to an acceptable diameter. Operation of this arrangement has been demonstrated experimentally, but only where the magnetic field experienced by the LINAC 9 is of sufficient homogeneity. This is difficult to achieve when the LINAC is positioned close to the main magnet coils, as the electron beam quality may be degraded by variations in the magnetic field experienced by the electron beam due to variations in magnetic field orientation and strength. The magnetic resonance imaging part is designed to generate a homogeneous magnetic field in a central imaging region, and the magnetic field in the volume occupied by the LINAC 9 is rather less homogeneous. The magnetic field will be strong within the bore of the main magnet 10, but the magnetic field lines in the region will not be truly parallel, particularly near the end of the magnet, and some deflection and dispersion of the beam will result.

The arrangement of FIG. 1 does not allow much space for radiation beam shaping devices such as multi-leaf collimator (MLC) conventionally and advantageously provided in radiation therapy equipment.

SUMMARY OF THE INVENTION

The present invention accordingly addresses at least some of these disadvantages and provides combined MRI and radiation therapy equipment as described below.

According to the present invention, the LINAC required for generating an electron beam, which is in turn required for generating a radiation beam, is located radially outside of the main magnet, and accordingly allows the diameter of the main magnet coils to be reduced.

The invention is applicable to actively-shielded solenoidal magnets, wherein shield coils of diameter greater than the main coils, but arranged coaxially with the main magnet coils, carry a current in the opposite direction as compared to a current carries by the main magnet coils. As is well known to those skilled in the art, such shield coils reduce the magnitude of a stray field around the MRI system. Preferably, the LINAC is arranged parallel to the axis of the main magnet, radially positioned between the radially outer surface of the main magnet coils and the radially inner surface of the shield coils. In this way, the combined MRI and radiation therapy equipment of the present invention has an outer diameter similar to that of a comparable MRI system, allowing installation in locations which would be impractical for a conventional combined MRI and radiation therapy system.

DESCRIPTION OF THE PREFERRED EMBODIMENTS

Figure 2:
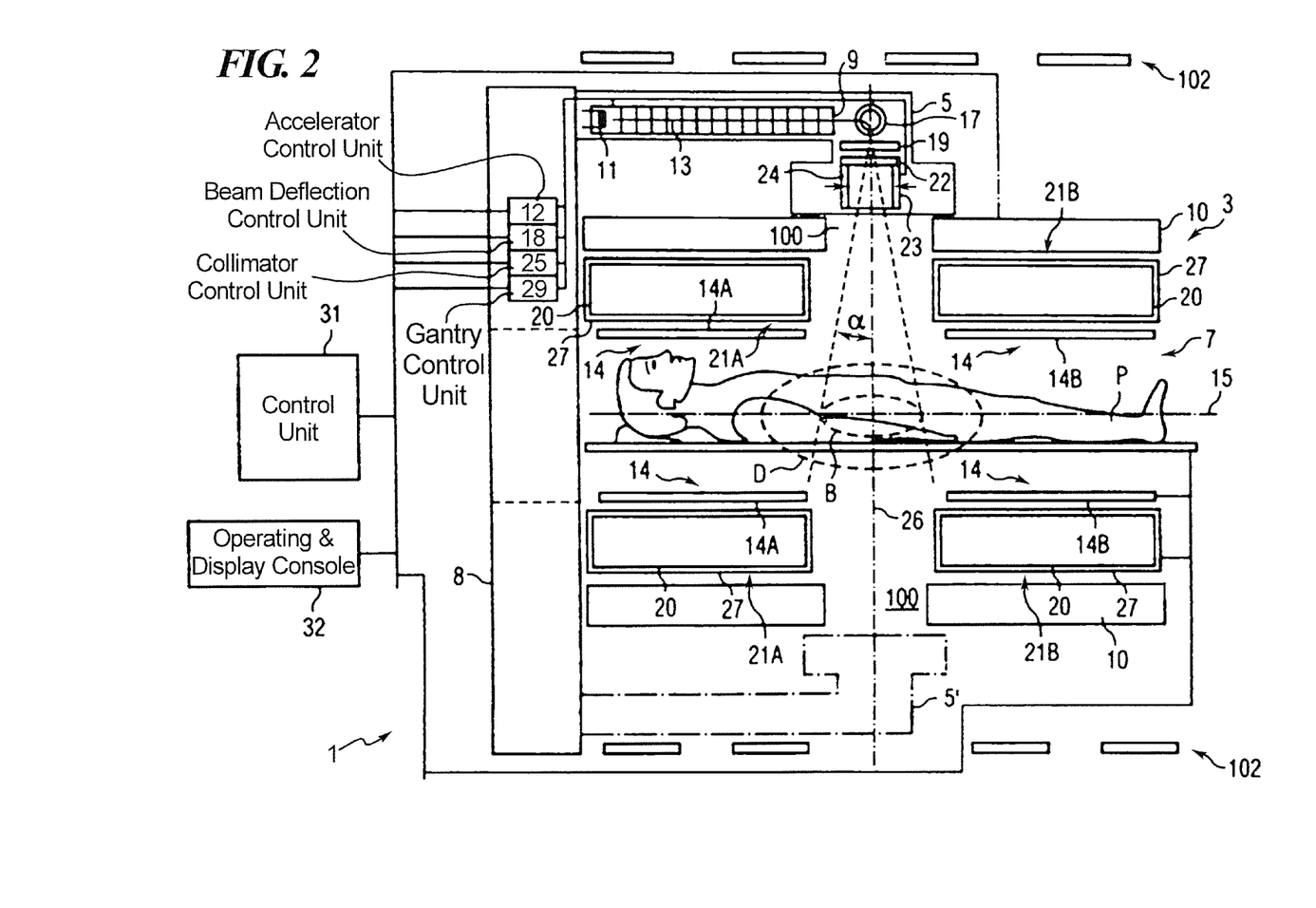
FIG. 2 shows a combined MRI and radiation therapy system 2 according to an embodiment of the present invention.

FIG. 2 shows a combined MRI and radiation therapy system 2 according to an embodiment of the present invention. Main magnet 10 is provided with "Letterbox" slots 100 through the cryostat and between coils of the main magnet to allow the radiation beam to reach a patient P at the irradiation center B. There may be some circumferential positions which are not available for passage of the radiation beam, for example where mechanical support pillars join the two parts of main magnet 50 together, but a good range of operation may be provided for without difficulty. LINAC 9, target 19 and collimator 23 are provided radially outside of the main magnet 10, but radially inside shield coils 102. In an embodiment of the invention, shield coils are placed inside the same cryostat as the main magnet, with a recess formed in the cryostat to accommodate the LINAC 9 and associated equipment. Gantry 8 is able to rotate about axis 15, enabling the radiation beam to be applied to the irradiation center B from an arbitrary angle. At intervals around the circumference of main magnet 10, the two parts shown in FIG. 2 may be joined, to allow mechanical supports to link the coils of the main magnet, to retain the main magnet coils in their required relative positions. In alternative embodiments, the LINAC and associated equipment may be fixed in position relative to the main magnet, and the main magnet with the LINAC and associated equipment may rotate about axis 15 to provide the radiation beam from a desired direction.

As the LINAC is positioned radially further from the irradiation center B, a collimator 23 similar to that used in the prior art system of FIG. 1 can direct a treatment beam over a wider proportion of a patient for a given beam angle α, when used according to the present invention, as the collimator 23 is positioned radially further from the irradiation center B, and axis 15. On the other hand, a smaller beam angle α' is required to cover the same irradiation center B as in the prior art, as illustrated in FIG. 1.

This arrangement provides significantly more space for the LINAC and associated equipment such as a multi-leaf collimator 23 than was the case with the prior art arrangement of FIG. 1. The main magnet coils are of smaller diameter than in the arrangement of WO2012049466, US2011/0213239A1 and GB2484529, and the system as a whole requires much less radial space than in the example of WO2003008986.

The electron deflector 17 may provide a simple transverse magnetic field, or an arrangement of coils as provided in US2011/0213239A1, or as in WO2012049466 and GB2484529. Permanent magnets may be used, preferably in a Halbach array, which does not generate an appreciable stray field. Beam-focusing elements may advantageously be provided.

Another advantage of positioning the LINAC between the main magnet and the shield coils is that the LINAC is positioned in a region of lower magnetic field strength, as described in more detail below. By careful design of the shield coils 102, the magnetic field experienced by the LINAC 9 may be arranged parallel to the path of the electron beam within the accelerator 13, and so the electron beam will not be deflected by the magnetic field of the main magnet 10 or the shield coils 102.

Shield coils 102 carry electric current in the opposite direction to the current carried by the main coils in main magnet 10. They generate an opposing magnetic field which reduces a stray field outside of the shield coils, and directs the return path of the main magnetic field between the magnet 10 and the shield coils 102. The magnetic field lines in this region are more parallel than those at the end of the bore of the main magnet, and the field strength is lower. By positioning the LINAC 9 within this region of lower-strength, more-parallel magnetic field, influence of the background magnetic field on the beam 13 is reduced. Preferably, in the present invention, the LINAC experiences a magnetic field which is parallel to the direction of the beam 13.

RF shielding may be provided around the LINAC to reduce its interference with the operation of magnetic resonance imaging.

More space is available for positioning of a multi-leaf collimator 23, which may accordingly be a better collimator with more leaves than could be accommodated in the arrangement of the prior art. As the magnetic field experienced by the collimator in the arrangement of the present invention is of lower strength than that experienced by the collimator in conventional arrangements such as shown in FIG. 1, the collimator 23 in the present invention may more easily be operated in the magnetic field of the main magnet 10.

The presence of the LINAC 9 and associated equipment in the proximity of the main magnet 10 will cause some distortion of the magnetic field in the imaging region. According to the present invention, the LINAC is positioned further from the imaging region, and so it has less of an influence on the magnetic field in the imaging region. It will be relatively simple to compensate for the remaining influence, for example by conventional shimming techniques, than would be the case in conventional arrangements such as in FIG. 1, where the LINAC is much closer to the imaging region.

Preferably, the LINAC and the electron beam deflector 17 are arranged such that the electron beam remains in a single plane. This simplifies modelling of the control of the electron beam. However, other deflectors, such as recited in US2011/0213239A1 may be used instead.

The beam deflection arrangement 17 may be provided by one or more permanent magnets. While such magnets will provide a strong field which will distort the imaging field, such distortion is static and should be relatively simple to correct for using conventional shimming methods. If a pulsed electro-magnet is used, current feed throughs will be required to carry electric current to the electromagnet, along with a cooling arrangement and a power supply capable of switching the required current at high frequencies. High-frequency switching of current to such an electro-magnet may cause mechanical vibration, and hence acoustic noise which is unpleasant for the patient and may cause mechanical deterioration of the equipment. Some of this vibration may be damped by enclosing the LINAC within a vacuum vessel, but is may be found simpler are more cost-effective to use a permanent magnet for beam deflection arrangement 17, and to correct the attendant distortion of the imaging field by conventional shimming.

In alternative embodiments, it may not be necessary to provide slots 100 in the cryostat for the passage of the radiation beam. If the cryostat is formed from an appropriate material, such as 10 mm thick aluminium, rather than the conventional 3 mm stainless steel, at least in the appropriate region, the radiation beam may be directed through the cryostat. This may enable a much simpler mechanical assembly.

As is conventional with combined MRI and radiation therapy systems, the MRI magnet of the present invention may provide a relatively low strength background field. For example, the main magnet may provide a background field of strength (flux density) 0.5 T or less. Field strengths (flux densities) of this level and below are believed to have reduced tendency to cause damage to peripheral tissue in combined MRI and radiation therapy systems.

An [example] exemplary design method may include the steps of:
- define centerline of LINAC and set a maximum tolerable deviation of field strength experienced by the LINAC;
- constrain imaging volume
- constrain stray field to ensure that the shielding coils remain effective
- constrain the geometry of the coils according to the design parameters of the system
- perform computer-aided optimization based on well-known linear optimization or linear current density optimizer methods.

Other optimization methods may be used, for example current density optimizers based on a simplex method.

Active Shielding Coil Design

In the example discussed above, and shown in FIG. 2, active shielding coils 102 are provided.

Assuming that the shield coils 102 provide "perfect" shielding, then the amount of magnetic flux inside the bore of the solenoidal main magnet 10 equals the amount of magnetic flux between the main coils and the shield coils. The flux within the bore is distributed over the cross-sectional area of the bore, while the flux between the main magnet coils and the shield coils is distributed over the annular cross-section of the region between the main coils and the shield coils.

Where the magnetic flux density in the bore is $B_0$,
the magnetic flux density in the region between the main coils and the shield coils is $B_a$,
$R_0$ is the average radius of the main magnet coils
$R_s$ is the average radius of the shield coils, $$B_a \approx B_0 \cdot R_0^2 / (R_s^2 - R_0^2).$$

If, for example, $R_s = 2R_0$, then $B_a = -B_0/3$. The arrangement of the present invention locates the LINAC 9 within a region of magnetic field strength one-third of that experienced by the LINAC in the prior art of FIG. 1. In an example magnet where $B_0 = 0.5$ T, the return flux density $B_a = -166$ mT. In a magnetic field of this flux density, drive motors for leaves of a multi-leaf collimator may be locally shielded, and it becomes a practical proposition to provide a multi-leaf collimator in a combined MRI and radiation therapy system, enabling active shaping of the radiation beam.

An appropriate magnet design can be achieved using a simplex current density optimizer, where the magnetic field along the LINAC is constrained between minimum and maximum values.

Figure 3:
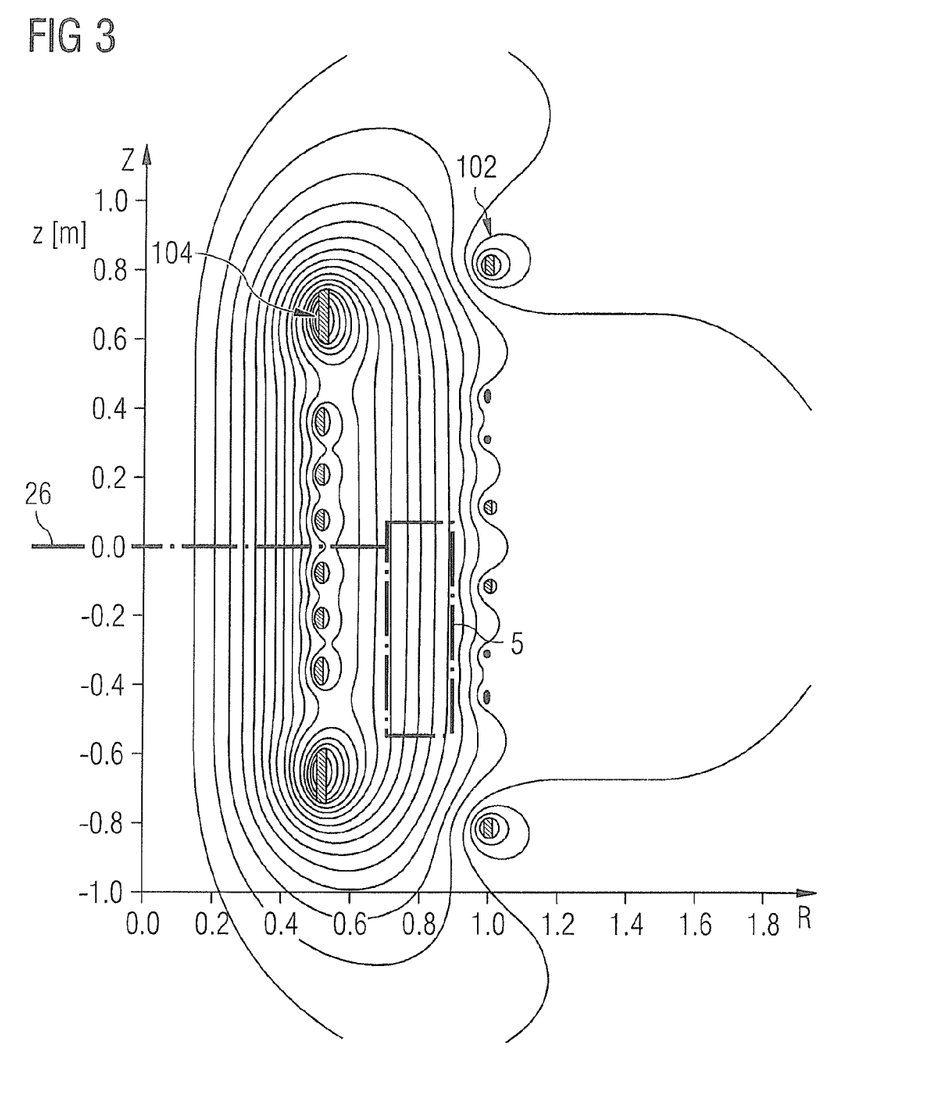
FIG. 3 shows an example design of such a magnet, in half-cross-section.

FIG. 3 shows an example deign of such a magnet, in half-cross-section symmetrical about axis 15. As is clear from FIG. 3, more than the usual number of shield coils 102 are provided, each of relatively few turns. This enables the magnetic field in the region between main magnet coils 104 and shield coils 102 to be relatively homogenous in the region of the LINAC and target assembly 5. Direction Z represents axial distance from the mid-plane of the magnet, and beam path 26. Direction R represents radial distance from the axis 15. The design must also meet the specified criteria for magnetic field shielding, typically restricting the stray field to no more than 5 gauss at a distance of 2.5 m radially and 4.5 m axially from the center point of the magnet.

Figure 4:
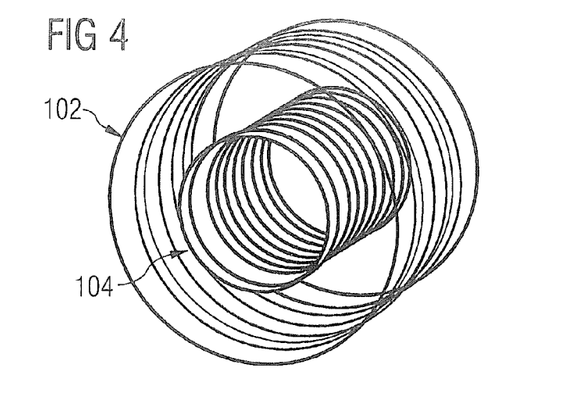
FIG. 4 shows a three-dimensional representation of the main magnet coils and shield coils of the design of FIG. 3.

FIG. 4 shows a three-dimensional representation of the main magnet coils 104 and shield coils of the design of FIG. 3.

Figure 5:
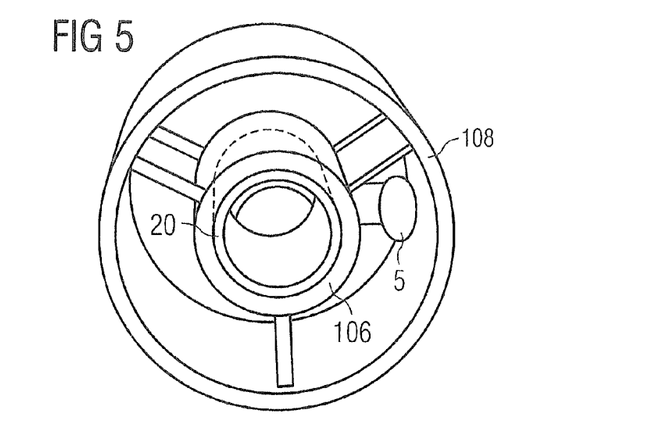
FIG. 5 shows a magnet of such a design in a more complete state.

FIG. 5 shows a magnet of such a design in a more complete state. The main magnet coils are located within an inner cryostat 106, while the shield coils are located within an outer cryostat 108. A gradient coil assembly 20 is provided within the bore of inner cryostat 106. The LINAC, its target and associated equipment are provided at 5, radially positioned between the inner cryostat and the outer cryostat. RF (body) coils and a patient will be positioned within the bore of the gradient coil assembly 20 when the system is used for imaging and radiation therapy treatment. In some embodiments, gaps such as "letterbox" slots are provided through the inner cryostat 106 to allow access for the radiation to the irradiation center B. In other embodiments, the radiation is directed through "windows" formed in the material of the cryostat. Such "windows" are of material with relatively low atomic number, such as aluminium.

It is highly desirable that the radiation source, formed by LINAC 9, target 19 and associated equipment in LINAC assembly 5, should be able to rotate about axis 15. This may be achieved in several alternative ways. For example, the LINAC assembly 5 may be fixed to the cryostats, and the whole assembly may be rotated about axis 15. A "letterbox" slot may be provided through the inner cryostat to accommodate the path of the radiation beam. Alternatively, the cryostats may be fixed in position, while the LINAC assembly 5 is arranged to rotate about the inner cryostat, within the outer cryostat. At least an "equatorial region" of the inner cryostat—that is, a circumferential band sufficient to accommodate all required paths of the radiation beam—contains one or more apertures of is formed of a material that is transparent to the radiation, and is devoid of main magnet coils. This may be conveniently achieved by forming the cryostat 106 of aluminium, and forming the necessary internal coil supporting structure of a composite material such as resin-impregnated carbon fiber, carbon fiber in a carbon matrix or TUFNOL® laminates. The chosen composite material should be evaluated for its radiation hardness to ensure that it will not suffer from structural degradation when exposed to the expected radiation.

Example of Passive Shielding

In an alternative series of embodiments, magnetic shielding and homogenisation of the magnetic field experienced by the LINAC assembly is provided not by shield coils but by passive shielding arrangements.

Figure 6:
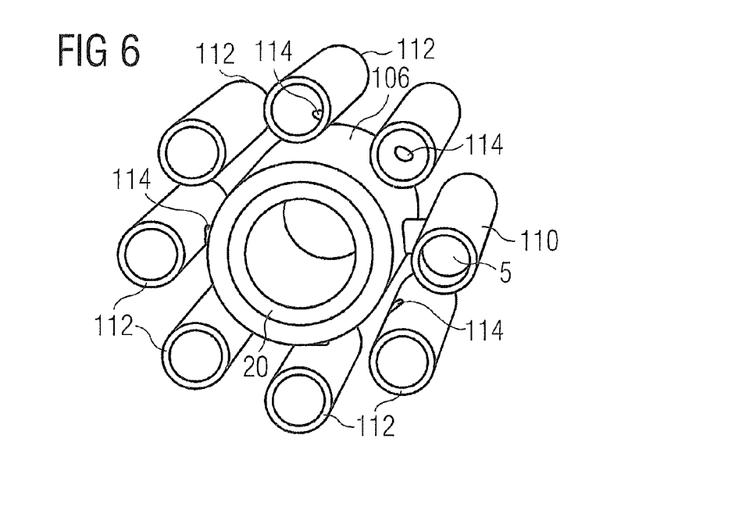
FIG. 6 illustrates a three-dimensional representation of a combined MRI magnet and radiation therapy LINAC assembly according to an embodiment of the present invention.

FIG. 6 illustrates a three-dimensional representation of a combined MRI magnet and radiation therapy LINAC assembly according to such an embodiment of the present invention.

Those features corresponding to features of FIG. 5 carry corresponding reference numbers. Instead of active shield coils within a cryostat, the embodiment of FIG. 6 has a ferromagnetic tube 110 arranged around the LINAC assembly 5, with a radial hole cut into it to accommodate the target and related equipment. This ferromagnetic tube prevents the high-frequency intermittent electron beam of the LINAC from interfering with the imaging system. It also isolates the LINAC assembly 5 from the magnetic field of the main magnet 10 to ensure that the residual field of the main magnet will not impair proper operation of the LINAC. Such a tube would need to be substantial—for example, having a wall thickness of 50 mm or more. It deforms the imaging field of the main magnet and restrains the stray field. In order to correct the deformation of the main magnet field, and to provide effective shielding of the stray field, similar ferromagnetic tubes 112 are placed at selected symmetrical circumferential locations about the main magnet coils.

In the illustrated arrangement, eight similar tubes are placed around the cryostat 106. More, or fewer, may be provided as will be determined during the design stage. For symmetry, all ferromagnetic tubes 110, 112 may have holes 114 that are similar to that provided to accommodate the target and related equipment in ferromagnetic tube 110. The holes 114 are preferably aligned with the axial position of the radiation path 26, and the axial center plane of the magnet. Alternatively, the holes may be at symmetrical axial positions about a mid point, alternately for adjacent tubes, to help with homogeneity of the imaging field.

In a simpler version, the additional ferromagnetic tubes 112 are placed with simple ferromagnetic rods of suitable dimensions around the main magnet coils, in positions and number determined by modelling.

While the present invention has been described with reference to a limited number of particular embodiments, numerous variations and modifications will be apparent to those skilled in the art. For example, radiation of different wavelengths may be used, such as gamma rays or x-rays. Different mechanisms for beam shaping and direction may be employed. Shielding arrangements other than the particular active and passive shielding arrangements described and illustrated can be used.

Although modifications and changes may be suggested by those skilled in the art, it is the intention of the inventor to embody within the patent warranted hereon all changes and modifications as reasonably and properly come within the scope of his contribution to the art.

I claim as my invention:

1. A combined magnetic resonance imaging (MRI) and radiation therapy system, comprising:
    MRI imaging equipment configured to acquire magnetic resonance data from a region of an examination subject;
    radiation therapy equipment configured to apply therapeutic radiation to at least a portion of said region;
    said MRI imaging equipment comprising a shielded solenoidal magnet comprising a plurality of main magnet coils arranged coaxially along an axis, and a magnetic shielding arrangement arranged coaxially with respect to said axis, at a larger radius from said axis than said plurality of main magnet coils;
    said radiation therapy equipment comprising a LINAC assembly, said LINAC assembly comprising a linear electron accelerator that accelerates electrons in an electron beam along an electron beam path that is parallel to said axis, a target, and a beam deflection arrangement that deflects electrons from said electron beam onto said target to produce a beam of said therapeutic radiation from said target; and
    said linear electron accelerator being located at a position radially between said main magnet coils and said magnetic shielding arrangement.

2. A combined MRI and radiation therapy system as claimed in claim 1, wherein said shielding arrangement comprises a plurality of shield coils that are coaxial with said main magnet coils.

3. A combined MRI and radiation therapy system as claimed in claim 1 comprising a cryostat in which said main magnet coils are contained, said cryostat comprising slots therein located in a path of said beam of therapeutic radiation, said slots allowing said beam of therapeutic radiation to pass between said main magnet coils.

4. A combined MRI and radiation therapy system as claimed in claim 1 comprising a cryostat in which said main magnet coils are contained, said cryostat comprising a window of material that is transparent to said therapeutic radiation located in a path of said beam of therapeutic radiation, That allows said beam of therapeutic radiation to pass between said main magnet coils.

5. A combined MRI and radiation therapy system as claimed in claim 1 comprising an annular cryostat in which said main magnet coils are contained, and a rotatable gantry in which said LINAC assembly is mounted, said gantry being configured to rotate said LINAC assembly around said main magnet coils in said annular cryostat, and said annular cryostat comprising a circumferential annular band composed of material that is transparent to said therapeutic radiation and an annulis within said cryostat, that is aligned with said circumferential band, that is devoid of said main magnet coils, said circumferential band and said annulis having a width along said axis that permits all selected widths of said therapeutic radiation beam to pass there through unimpeded.

6. A combined MRI and radiation therapy system as claimed in claim 5 wherein said shielding arrangement comprises a plurality of shield coils that are coaxial with said main magnet coils, and comprising a cryostat in which said main magnet coils and said shield coils are contained, said cryostat having a recess therein at a radial position between said main magnet coils and said shield coils in which said LINAC assembly is rotated by said gantry throughout an entire path of rotation of said LINAC assembly.

7. A combined magnetic resonance imaging (MRI) and radiation therapy system, comprising:
    MRI imaging equipment configured to acquire magnetic resonance data from a region of an examination subject;
    radiation therapy equipment configured to apply therapeutic radiation to at least a portion of said region;
    said MRI imaging equipment comprising a shielded solenoidal magnet comprising a plurality of main magnet coils arranged coaxially along an axis, and a magnetic shielding arrangement arranged coaxially with respect to said axis, at a larger radius from said axis than said plurality of main magnet coils;
    said radiation therapy equipment comprising a LINAC assembly, said LINAC assembly comprising a linear electron accelerator that accelerates electrons in an electron beam along an electron beam path that is parallel to said axis, a target, and a beam deflection arrangement that deflects electrons from said electron beam onto said target to produce a beam of said therapeutic radiation from said target; and
    said magnetic shielding arrangement comprising a ferromagnetic tube that surrounds said LINAC assembly, said ferromagnetic tube having a radial opening therein in which at least said target is arranged.

8. A combined MRI and radiation therapy system as claimed in claim 7 wherein said shielding arrangement comprises a plurality of additional ferromagnetic tubes, substantially identical to said ferromagnetic tube, said ferromagnetic tube and said plurality of substantially identical ferromagnetic tubes being respectively located at selected circumferential locations around said main magnet coils.

9. A combined MRI and radiation therapy system as claimed in claim 7 wherein said shielding arrangement comprises ferromagnetic rods at selected positions around said main magnet coils.

10. A combined MRI and radiation therapy system as claimed in claim 7 comprising a cryostat in which said main magnet coils are contained, said cryostat comprising slots therein located in a path of said beam of therapeutic radiation, said slots allowing said beam of therapeutic radiation to pass between said main magnet coils.

11. A combined MRI and radiation therapy system as claimed in claim 7 comprising a cryostat in which said main magnet coils are contained, said cryostat comprising a window of material that is transparent to said therapeutic radiation located in a path of said beam of therapeutic radiation, that allows said beam of therapeutic radiation to pass between said main magnet coils.

12. A combined MRI and radiation therapy system as claimed in claim 7 comprising an annular cryostat in which said main magnet coils are contained, and a rotatable gantry in which said LINAC assembly is mounted, said gantry being configured to rotate said LINAC assembly around said main magnet coils in said annular cryostat, and said annular cryostat comprising a circumferential annular band composed of material that is transparent to said therapeutic radiation and an annulis within said cryostat, that is aligned with said circumferential band, that is devoid of said main magnet coils, said circumferential band and said annulis having a width along said axis that permits all selected widths of said therapeutic radiation beam to pass there through unimpeded.

\* \* \* \* \*